(12) United States Patent
Liu et al.

(10) Patent No.: US 10,745,363 B2
(45) Date of Patent: Aug. 18, 2020

(54) CRYSTAL FORMS OF VALSARTAN DISODIUM SALT

(71) Applicant: NORATECH PHARMACEUTICALS, INC., Taipei (TW)

(72) Inventors: Fei Liu, Nanjing (CN); Gang Wu, Nanjing (CN); Weiming Jiang, Nanjing (CN); Cheng-Gang Lin, Nanjing (CN); Xuan Cai, Nanjing (CN); Ping Lin, Nanjing (CN); Yuling Lu, Nanjing (CN); Lixiang Liu, Nanjing (CN)

(73) Assignee: NANJING NORATECH PHARMACEUTICALS CO., LTD, Nanjing (CN)

( * ) Notice: Subject to any disclaimer, the term of this patent is extended or adjusted under 35 U.S.C. 154(b) by 0 days.

(21) Appl. No.: 16/329,992

(22) PCT Filed: Sep. 2, 2016

(86) PCT No.: PCT/CN2016/097926
§ 371 (c)(1),
(2) Date: Mar. 1, 2019

(87) PCT Pub. No.: WO2018/040065
PCT Pub. Date: Mar. 8, 2018

(65) Prior Publication Data
US 2019/0194149 A1     Jun. 27, 2019

(51) Int. Cl.
*C07D 257/04*     (2006.01)
*A61P 9/12*       (2006.01)
*A61K 31/41*      (2006.01)
*A61P 9/10*       (2006.01)
*A61P 9/04*       (2006.01)

(52) U.S. Cl.
CPC ............ *C07D 257/04* (2013.01); *A61K 31/41* (2013.01); *A61P 9/04* (2018.01); *A61P 9/10* (2018.01); *A61P 9/12* (2018.01); *C07B 2200/13* (2013.01)

(58) Field of Classification Search
CPC ... A61K 31/41; A61P 9/04; A61P 9/10; A61P 9/12; C07B 2200/13; C07D 257/04
See application file for complete search history.

(56) References Cited

U.S. PATENT DOCUMENTS

| | | |
|---|---|---|
| 5,399,578 A | 3/1995 | Bühlmayer et al. |
| 8,278,339 B2 | 10/2012 | Marti et al. |
| 10,588,892 B2 * | 3/2020 | Dymacek ............... A61K 31/41 |
| 2003/0207930 A1 * | 11/2003 | Marti ...................... A61P 9/08 |
| | | 514/381 |

(Continued)

FOREIGN PATENT DOCUMENTS

| CN | 1443176 A | 9/2003 |
|---|---|---|
| CN | 102596899 A | 7/2012 |

(Continued)

OTHER PUBLICATIONS

International Search Report, issued in PCT/CN2016/097926, dated May 31, 2017.

*Primary Examiner* — Valerie Rodriguez-Garcia
(74) *Attorney, Agent, or Firm* — Birch, Stewart, Kolasch & Birch, LLP

(57) ABSTRACT

Provided are crystal forms A, B, D, E, F, G and H of valsartan disodium salt and a preparation method therefor.

29 Claims, 18 Drawing Sheets

(56) References Cited

U.S. PATENT DOCUMENTS

2012/0238761 A1    9/2012  Sedelmeier et al.
2016/0324821 A1    11/2016  Feng et al.

FOREIGN PATENT DOCUMENTS

| CN | 102702119 A | 10/2012 |
|---|---|---|
| EP | 0 443 983 A1 | 8/1991 |
| WO | Wo 2008/018843 A1 | 2/2008 |
| WO | WO 2016/074651 A | 5/2016 |
| WO | WO 2016/125123 A1 | 8/2016 |

* cited by examiner

CRYSTAL FORMS OF VALSARTAN DISODIUM SALT

TECHNOLOGY FIELD

The present invention relates to the field of pharmaceutical synthesis, particularly to new crystalline forms A, B, D, E, F, G and H of valsartan disodium salts and a preparation method thereof.

BACKGROUND OF THE INVENTION

Valsartan (Formula I) is a specific angiotensin (AT) II receptor antagonist that selectively acts on the $AT_1$ receptor subtype without any agonist activity.

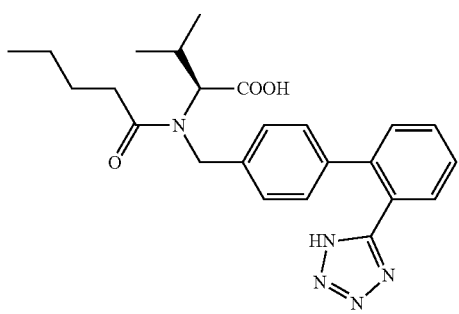

(I)

Valsartan is a drug that has very low bulk density and is insoluble in water. The melting point of the free acid form of valsartan is 80-95° C. in the closed crucible, 105-110° C. in the open crucible, and the enthalpy of fusion is 12 kJ/mol. The melting point and the measured melting enthalpy of 12 kJ/mol demonstrated the poor stability of the valsartan particles in the free acid form.

A more stable form of valsartan is required during the process of drying or milling, as well as during the preparation of the formulation. Valsartan is a free acid having two acidic hydrogen atoms, one attaching to a carboxyl group and the other attaching to a tetrazole ring. Therefore, an acidic hydrogen atom or two acidic hydrogen atoms can be replaced with a monovalent or divalent cation. Valsartan sodium salt can improve the solubility of valsartan in solution, but it is hygroscopic and needs to be stored in a cool and dry environment. The valsartan disodium salt disclosed in CN01813039.9 is known to have a melting point starting from 260 and becoming brown at 295. The sodium salt is analyzed by elemental analysis, and the obtained substance (hygroscopic) can be equilibrated in air ($C_{24}H_{27}N_5O_3Na_2$, 5.36 mol $H_2O$, molar mass 576.05), from which it is known that the sodium salt has a hygroscopicity of up to 20%. It needs to further study the solid form of valsartan sodium salt in order to obtain the valsartan sodium salt with improved physical properties such as solubility and hygroscopicity.

It is difficult to form a salt of valsartan having the desired advantageous properties, however, the crystalline forms of the valsartan disodium salt in the present invention exhibit the desired improved properties.

SUMMARY OF THE INVENTION

An objective of the present invention is to provide crystalline forms A, B, D, E, F, G and H of valsartan disodium salts.

Another objective of the present invention is to provide a process for the preparation of crystalline forms A, B, D, E, F, G and H of valsartan disodium salts.

The crystalline form A of valsartan disodium salts of the present invention is characterized in that: by using a Cu-Kα radiation, its X-ray powder diffraction spectrum shows peaks (expressed in degrees 2θ) at about 4.7±0.2, 8.5±0.2, 9.5±0.2. 13.6±0.2, 15.4±0.2, 16.5±0.2, 18.1±0.2, 19.9±0.2, 22.0±0.2, 22.4±0.2, 23.3±0.2, 23.8±0.2, 25.3±0.2, and 27.8±0.2; preferably at 4.7±0.2, 8.5±0.2, 9.5±0.2, 10.8±0.2, 11.0±0.2, 13.6±0.2, 13.8±0.2, 14.4±0.2, 15.4±0.2, 16.5±0.2, 18.1±0.2, 19.9±0.2, 22.0±0.2, 22.4±0.2, 23.3±0.2, 23.8±0.2, 25.3±0.2, 27.8±0.2, and 28.9±0.2.

In one embodiment, at a heating rate of 10° C./min, the crystalline form A of valsartan disodium salts has a differential scanning calorimetry thermogram showing an endothermic peak at around 183° C.

In one embodiment, at a heating rate of 10° C./min, the crystalline form A of valsartan disodium salts has a differential scanning calorimetry thermogram showing an endothermic peak at 182-184° C.

In one embodiment, the crystalline form A of valsartan disodium salts has an X-ray powder diffraction spectrum substantially the same as that shown in FIG. 1.

In one embodiment, at a heating rate of 10° C./min, the crystalline form A of valsartan disodium salts has an endothermic curve of differential thermal analysis substantially the same as that shown in FIG. 2.

In one embodiment, the crystalline form A of valsartan disodium salts is a non-solvate of valsartan disodium salt.

The DSC thermogram of the crystalline form A of valsartan disodium salts shows an endothermic peak at around 183° C., and the enthalpy value is 335.53 J/g. The crystalline form has a high endothermic peak temperature and a high enthalpy value, indicating that the crystalline lattice of the crystalline form has a high stability. It is worth noting that the water absorption is only 2.6% when maintaining the crystalline form in an open container at a temperature of 25±1° C. and a relative humidity of 43.5±2% for 3 hours.

The crystalline form B of valsartan disodium salts of the present invention is characterized in that: by using a Cu-Kα radiation, its X-ray powder diffraction spectrum shows peaks (expressed in degrees 2θ) at about 4.4±0.2 and 8.8±0.2.

In one embodiment, the crystalline form B of valsartan disodium salts has a melting point of about 198±5° C.

In one embodiment, at a heating rate of 10° C./min, the crystalline form B of valsartan disodium salts does not exhibit significant desolvation on the thermogravimetric analyzer.

In one embodiment, the crystalline form B of valsartan disodium salts is a non-solvate of the valsartan disodium salt.

In one embodiment, the crystalline form B of valsartan disodium salts has an X-ray powder diffraction spectrum substantially the same as that shown in FIG. 3.

In one embodiment, at a heating rate of 10° C./min, the crystalline form B of valsartan disodium salts has a weight loss curve substantially the same as the weight loss curve of thermogravimetric analysis shown in FIG. 4.

The crystalline form D of valsartan disodium salts of the present invention is characterized in that: by using a Cu-Kα radiation, its X-ray powder diffraction spectrum shows peaks (expressed in degree 2θ) at about 4.4±0.2, 9.0±0.2, 14.9±0.2. 21.4±0.2, and 22.4±0.2; preferably at about 4.4±0.2, 9.0±0.2, 12.6±0.2, 14.9±0.2, 15.4±0.2, 16.3±0.2, 17.8±0.2, 21.4±0.2, 22.4±0.2, and 23.8±0.2.

In one embodiment, the crystalline form D of valsartan disodium salts has a melting point of about 207±5° C.

In one embodiment, the crystalline form D of valsartan disodium salts has an X-ray powder diffraction spectrum substantially the same as that shown in FIG. 5.

In one embodiment, the crystalline form D of valsartan disodium salts is a non-solvate of valsartan disodium salts.

The crystalline form E of valsartan disodium salts of the present invention is characterized in that: by using a Cu-Ka radiation, its X-ray powder diffraction spectrum shows peaks (expressed in degree 2θ) at about 6.3±0.2, 12.3±0.2, 14.7±0.2, 16.5±0.2, and 17.4±0.2; preferably at 6.3±0.2, 9.8±0.2, 12.3±0.2, 14.7±0.2, 16.5±0.2, 17.4±0.2, 20.4±0.2, and 22.0±0.2.

In one embodiment, at a heating rate of 10° C./min, the crystalline form E of valsartan disodium salts has a differential scanning calorimetry thermogram showing an endothermic peak at around 127° C.

In one embodiment, at a heating rate of 10° C./min, the crystalline form E of valsartan disodium salts has a differential scanning calorimetry thermogram showing an endothermic peak at 107-127° C.

In one embodiment, at 64-200° C., the crystalline form E of valsartan disodium salts has a thermal weight loss of not less than 15%, preferably a thermal weight loss of not less than 16%, more preferably a thermal weight of not less than 17%, the most preferably a thermal weight loss of not less than 18%.

In one embodiment, the crystalline form E of valsartan disodium salts has an X-ray powder diffraction spectrum substantially the same as that shown in FIG. 6.

In one embodiment, at a heating rate of 10° C./min, the crystalline form E of valsartan disodium salts has a weight loss curve of thermogravimetric analysis substantially the same as that shown in FIG. 7.

In one embodiment, at a heating rate of 10° C./min, the crystalline form E of valsartan disodium salts has an endothermic curve of differential thermal analysis substantially the same as that shown in FIG. 8.

In one embodiment, the crystalline form E of valsartan disodium salts is a dioxane solvate of valsartan disodium salts.

In one embodiment, the ratio of valsartan disodium salt to dioxane in the crystalline form E of valsartan disodium salts is 1:1.

In one embodiment, the crystalline form E of valsartan disodium salts has a liquid-state nuclear magnetic spectrum as shown in FIG. 9.

The crystalline form F of valsartan disodium salts of the present invention is characterized in that: by using a Cu-Ka radiation, its X-ray powder diffraction spectrum shows peaks (expressed in degree 2θ) at about 6.2±0.2, 14.9±0.2, and 18.3±0.2; preferably at 6.2±0.2, 9.6±0.2, 12.3±0.2, 14.9±0.2, 16.6±0.2, 17.2±0.2, 18.3±0.2, 20.0±0.2, and 22.2±0.2.

In one embodiment, at a heating rate of 10° C./min, the crystalline form F of valsartan disodium salts has a differential scanning calorimetry thermogram showing an endothermic peak at around 116° C.

In one embodiment, at a heating rate of 10° C./min, the crystalline form F of valsartan disodium salts has a differential scanning calorimetry thermogram showing an endothermic peak at 104-117° C.

In one embodiment, at 55-150° C., the crystalline form F of valsartan disodium salts has a thermal weight loss of not less than 8.4%, preferably a thermal weight loss of not less than 10%, more preferably a thermal weight loss of not less than 11%.

In one embodiment, the crystalline form F of valsartan disodium salts has an X-ray powder diffraction spectrum substantially the same as that shown in FIG. 10.

In one embodiment, at a heating rate of 10° C./min, the crystalline form F of valsartan disodium salts has a weight loss curve of thermogravimetric analysis substantially the same as that shown in FIG. 11.

In one embodiment, at a heating rate of 10° C./min, the crystalline form F of valsartan disodium salts has an endothermic curve of differential thermal analysis substantially the same as that shown in FIG. 12.

In one embodiment, the crystalline form F of valsartan disodium salts is an ethyl acetate solvate of valsartan disodium salts.

In one embodiment, the ratio of valsartan disodium salt to ethyl acetate in the crystalline form F of valsartan disodium salts is 1:0.5.

In one embodiment, the crystalline form F of valsartan disodium salts has a liquid-state nuclear magnetic spectrum as shown in FIG. 13.

The crystalline form G of valsartan disodium salts of the present invention is characterized in that: by using a Cu-Ka radiation, its X-ray powder diffraction spectrum shows peaks (expressed in degree 2θ) at about 6.4±0.2, 8.3±0.2, 9.5±0.2, 17.3±0.2, and 19.4±0.2; preferably at 6.4±0.2, 8.3±0.2, 8.5±0.2, 9.5±0.2, 12.8±0.2, 17.3±0.2, 19.4±0.2, and 26.0±0.2.

In one embodiment, at a heating rate of 10° C./min, the crystalline form G of valsartan disodium salts has a superposition of degradation and melting signals in the differential scanning calorimetry curve.

In one embodiment, the crystalline form G of valsartan disodium salts has an X-ray powder diffraction spectrum substantially the same as that shown in FIG. 14.

In one embodiment, at a heating rate of 10° C./min, the crystalline form G of valsartan disodium salts has a weight loss curve of thermogravimetric analysis substantially the same as that shown in FIG. 15.

In one embodiment, at a heating rate of 10° C./min, the crystalline form G of valsartan disodium salts has an endothermic curve of differential thermal analysis substantially the same as that shown in FIG. 16.

In one embodiment, the crystalline form G of valsartan disodium salts is a non-solvate of valsartan disodium salts.

The crystalline form H of valsartan disodium salts of the present invention is characterized in that: by using a Cu-Ka radiation, its X-ray powder diffraction spectrum shows peaks (expressed in degree 2θ) at about 4.5±0.2, 8.7±0.2, and 9.0±0.2; preferably at 4.5±0.2, 8.7±0.2, 9.0±0.2, 15.4±0.2, 18.3±0.2, and 22.2±0.2; more preferably at 4.5±0.2, 8.7±0.2, 9.0±0.2, 15.4±0.2, 15.6±0.2, 18.3±0.2, 21.8±0.2, 22.2±0.2, and 26.3±0.2.

In one embodiment, at a heating rate of 10° C./min, the crystalline form H of valsartan disodium salts does not exhibit a significant desolvation on a thermogravimetric analyzer.

In one embodiment, the crystalline form H of valsartan disodium salts has an X-ray powder diffraction spectrum substantially the same as that shown in FIG. 17.

In one embodiment, at a heating rate of 10° C./min, the crystalline form H of valsartan disodium salts has a weight loss curve of thermogravimetric analysis substantially the same as that shown in FIG. 18.

In one embodiment, the crystalline form H of valsartan disodium salts is a non-solvate of valsartan disodium salt.

The crystalline form of valsartan disodium salts of the present invention has unexpectedly advantageous characteristics, and the crystalline salt has a clear endothermic peak with a significant endothermic enthalpy under given conditions. The crystalline salt of the present invention is stable, has good quality during storage, and does not change significantly in water content.

The present invention provides a pharmaceutical composition comprising a therapeutically effective amount of the said crystalline forms A, B, D, E, F, G and H of valsartan disodium salts in the present invention in combination with a pharmaceutically acceptable carrier, wherein the pharmaceutical composition can be enterally or parenterally administrated, and can be administered to a patient in the form of a tablet, capsule, solution, suspension or the like.

The crystalline forms A, B, D, E, F, G and H of valsartan disodium salts in the present invention, or a pharmaceutical composition comprising the same, can be used, for example, for preventing or treating a disease or condition which is susceptible to treatment by blocking the $AT_1$ receptor, wherein the disease or condition is selected from the group consisting of: hypertension, congestive heart failure, acute renal failure, chronic renal failure, restenosis after percutaneous transluminal angioplasty and restenosis after coronary artery bypass surgery; atherosclerosis, insulin resistance and syndrome X, type 2 diabetes, obesity, nephropathy, hypothyroidism, survival after myocardial infarction, coronary heart disease, senile hypertension, familial dyslipidemia, increased collagen formation, remodeling after fibrosis and hypertension, and all of these diseases or conditions associated with or unrelated to hypertension; endothelial dysfunction with or without hypertension; hyperlipidemia, hyperlipoproteinemia, atherosclerosis and hypercholesterolemia; and glaucoma.

The main application is in the treatment of hypertension and congestive heart failure as well as post-myocardial infarction.

A person skilled in the art is fully enabled to select a relevant standard animal experimental model to demonstrate the therapeutic indications and benefits indicated by the context.

In the present invention, the term "the same X-ray powder diffraction spectrum" refers to that the positions of the peaks represented by degrees 2θ are substantially the same, and the relative intensities of the peak positions are substantially the same, wherein the relative intensity refers to a ratio obtained by comparing the intensity of other peaks with the intensity of the strongest peak when the intensity of the peak having the highest intensity among all the diffraction peaks of the X-ray powder diffraction spectrum is set as 100%. It should be noted that the 2θ angle in the X-ray powder diffraction spectrum sometimes has a number of measurement errors due to various factors, and the measured value may usually vary to a degree of ±0.3; preferably ±0.2; and more preferably ±0.1. Therefore, in the present specification, the 2θ angle based on the measured value of a specific sample is understood to comprise these allowable errors. In the present invention, the term "substantially the same as that shown in FIG. 1" refers to at least 50%, or at least 60%, or at least 70%, or at least 80%, or at least 90, or at least 95%, or at least 99% of the peaks appear in the given X-ray powder diffraction spectrum.

It should be explained that the absorption peak in differential scanning calorimetry is an inherent physical property of each crystalline form of the present invention. However, in the actual measurement, in addition to measurement errors, impurities may be mixed in an allowable amount. The possibility of a change in the melting point is also undeniable. Therefore, a person skilled in the art can fully understand to what extent the measured value of the endothermic peak temperature in the present invention can be varied. For example, the conceivable error is, in some cases, about ±5° C.; preferably about ±3° C.; more preferably about ±2° C.; and most preferably about ±1° C.

In the present invention, the term "melting point" refers to the initial melting temperature at which the crystal form is melted.

The analysis methods used in the present invention are as follows:

1) X-Ray Powder Diffraction

A Bruker D8 advance diffractometer was used. At room temperature, a Cu Ka fill tube (40 kV, 40 mA) was utilized as an X-ray source with a wide-angle goniometer, and the diffractometer was equipped with a 0.6 mm divergence slit, a 2.5° primary Soller slit, a 2.5° secondary Soller slit, an 8 mm anti-scatter slit, a 0.1 mm detector slit, and a LynxEye detector. In the 2θ continuous scan mode, data was acquired with a scanning step of 0.02° at a scanning speed of 2.4°/min in the range of 3°-40°.

2) Differential Scanning Calorimetry

Data was acquired using a TA Q200 and a Mettler DSC 1+ before heating from room temperature to degradation temperature at a heating rate of 10° C./min, under the protection of $N_2$ flow at 50 mL/min.

3) Thermogravimetric Analyzer

Data was acquired using a TA Q500, and scans were performed from room temperature to until the sample was degradating to less than 30% at a heating rate of 10° C./min, under the protection of $N_2$ flow at 50 mL/min.

DETAILED DESCRIPTION OF THE INVENTION

Figure 1:
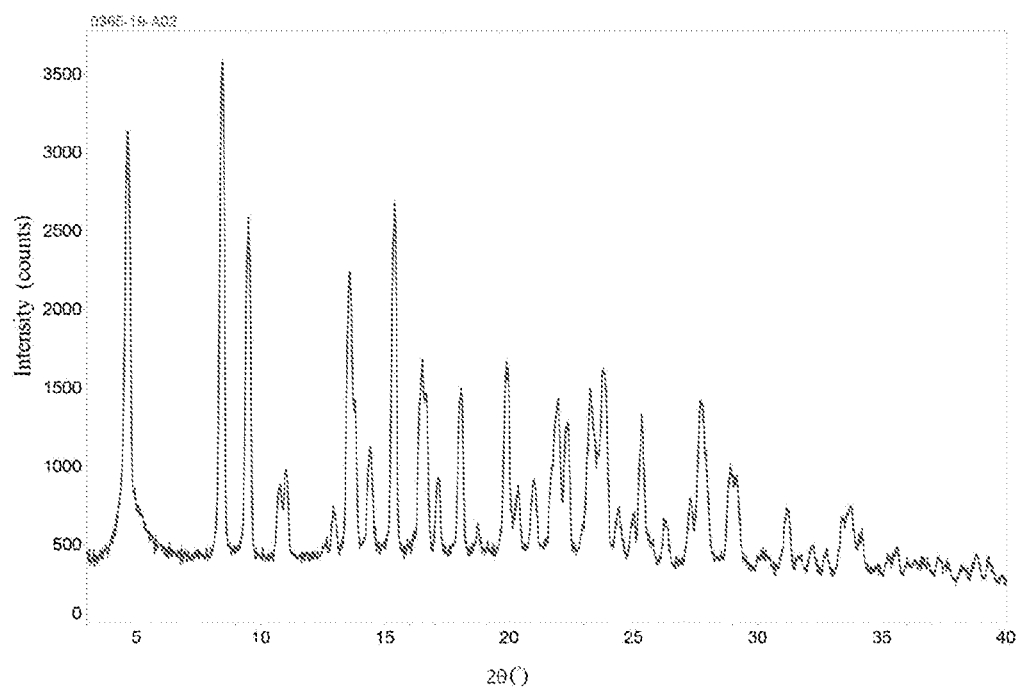
FIG. 1 shows an X-ray powder diffraction (XRD) pattern of a crystalline form A of valsartan disodium salts.
Figure 2:
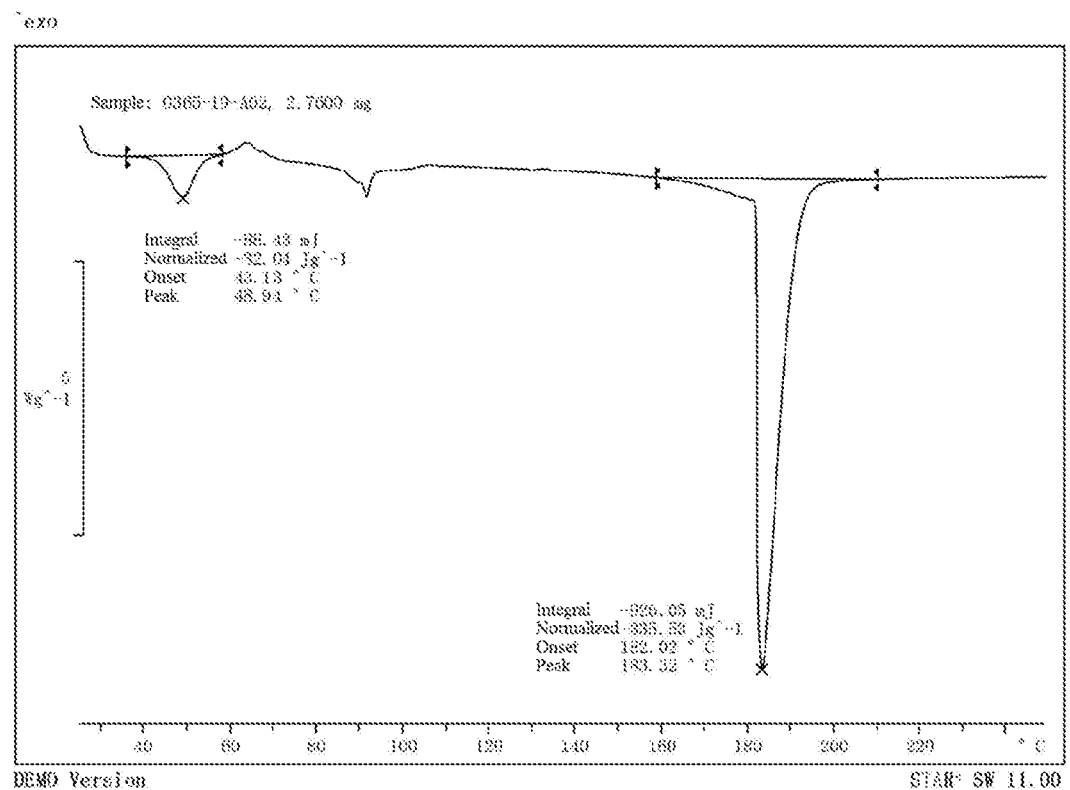
FIG. 2 shows a differential scanning calorimetry (DSC) thermogram of a crystalline form A of valsartan disodium salts.
Figure 3:
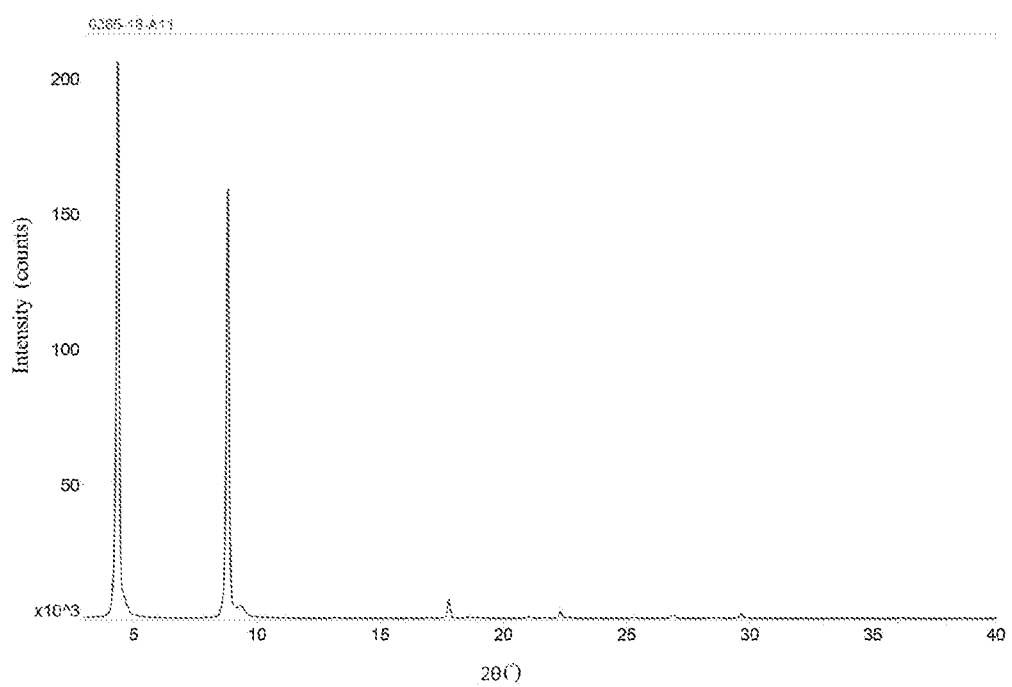
FIG. 3 shows an X-ray powder diffraction (XRD) pattern of a crystalline form B of valsartan disodium salts.
Figure 4:
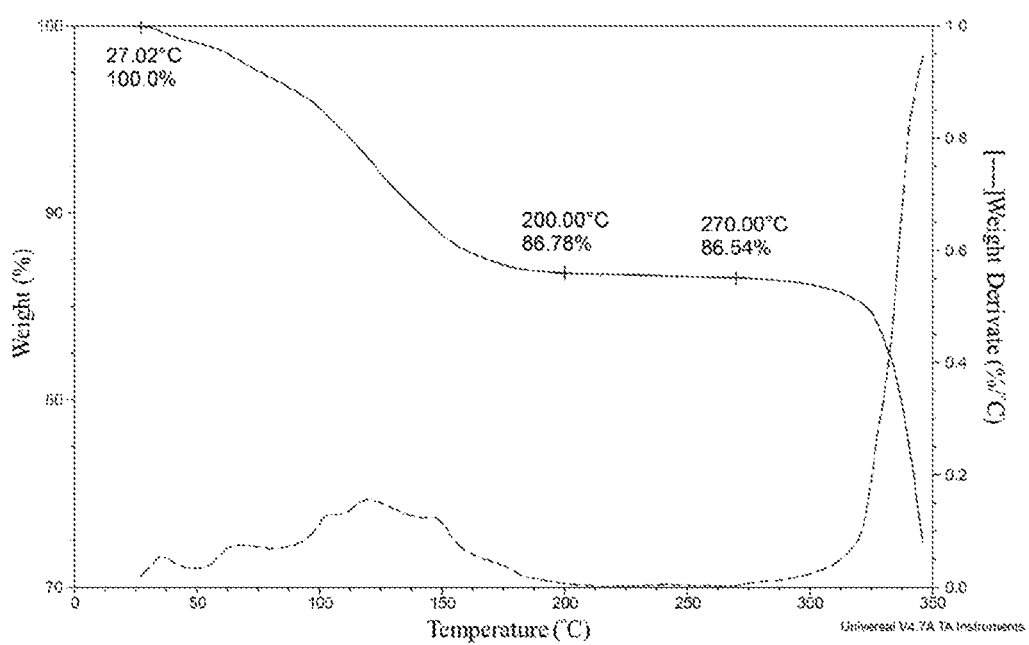
FIG. 4 shows a thermogravimetric analysis (TGA) plot of a crystalline form B of valsartan disodium salts.
Figure 5:
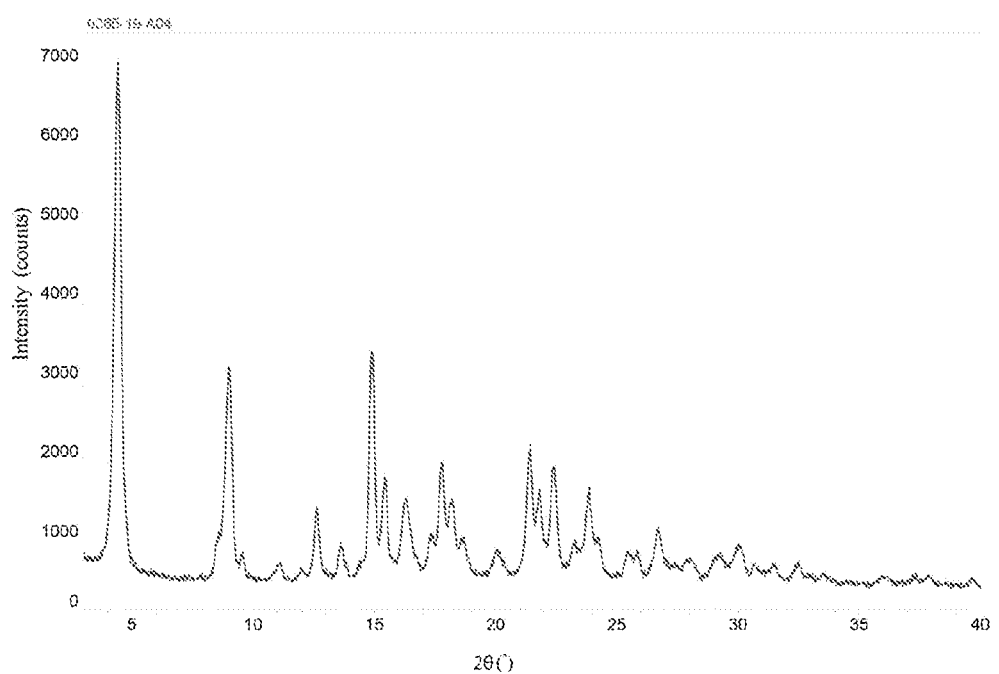
FIG. 5 shows an X-ray powder diffraction (XRD) pattern of a crystalline form D of valsartan disodium salts.
Figure 6:
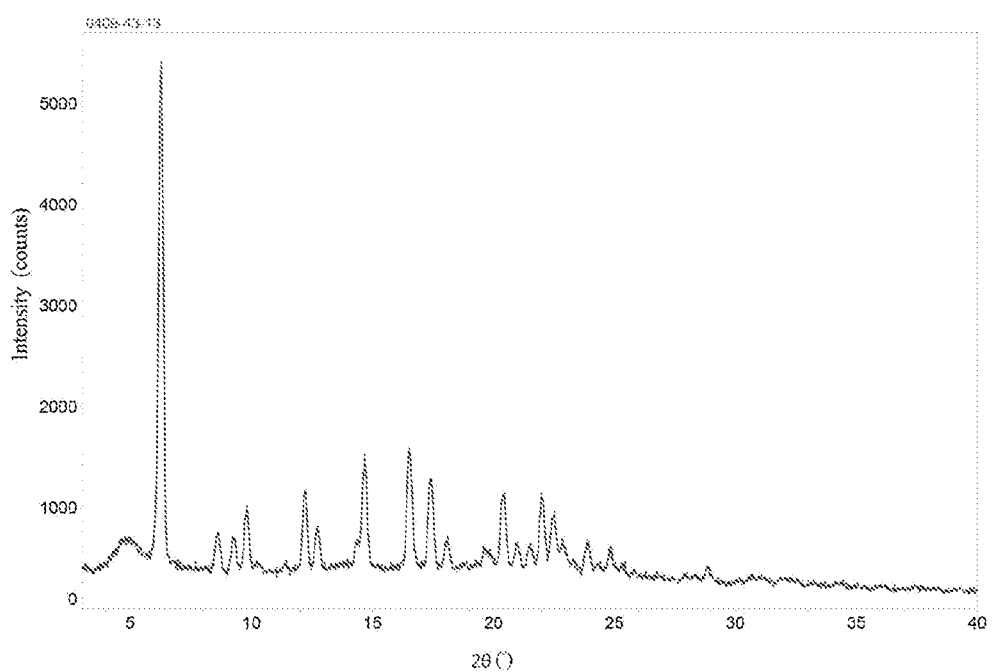
FIG. 6 shows an X-ray powder diffraction (XRD) pattern of a crystalline form E of valsartan disodium salts.
Figure 7:
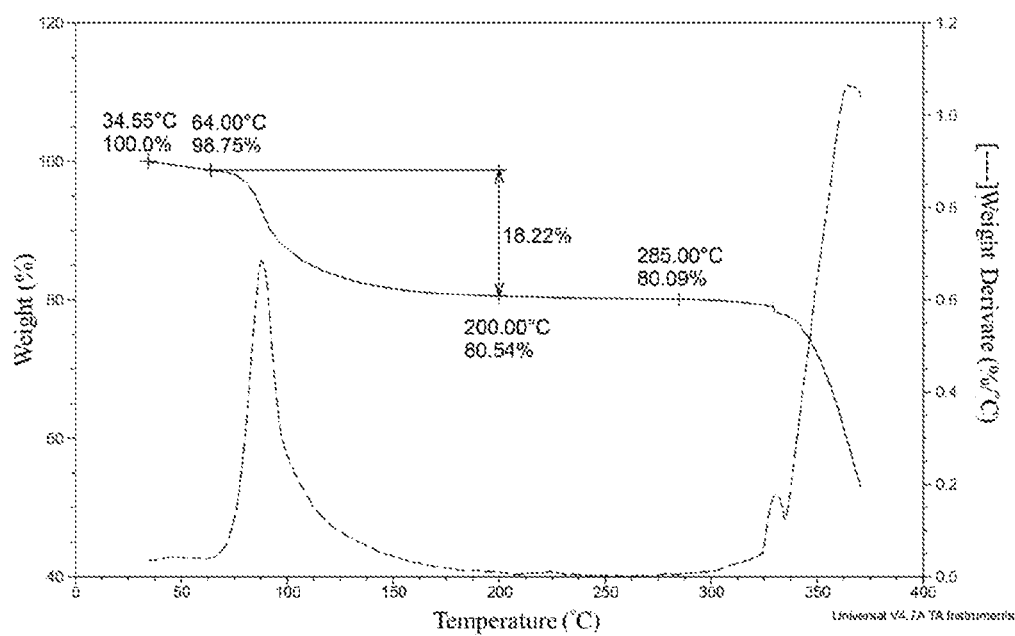
FIG. 7 shows a thermogravimetric analysis (TGA) plot of a crystalline form E of valsartan disodium salts.
Figure 8:
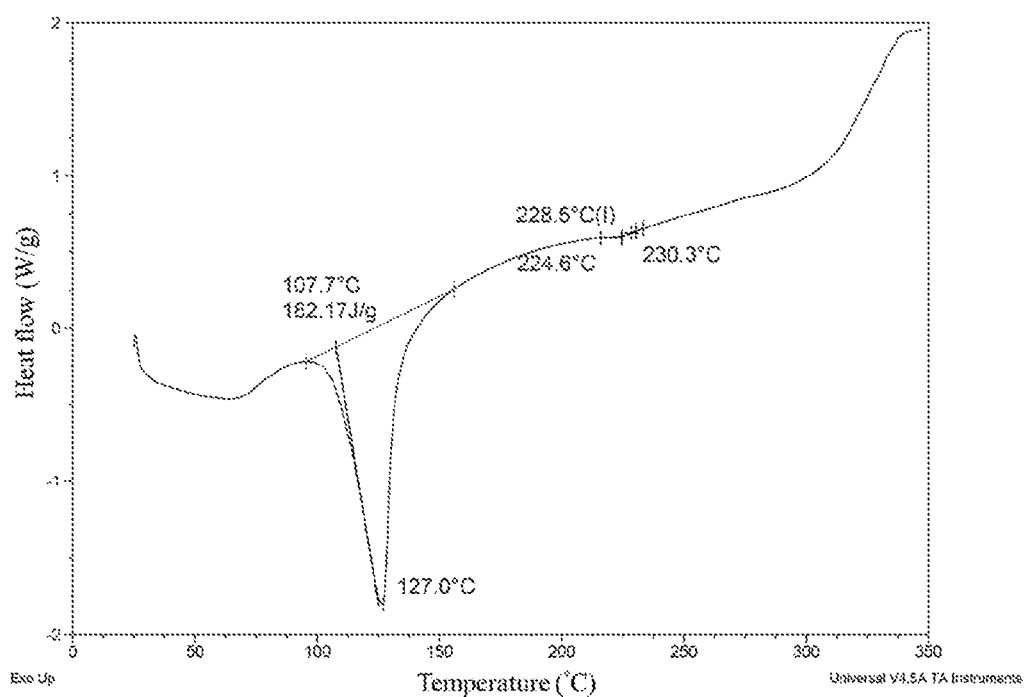
FIG. 8 shows a differential scanning calorimetry (DSC) thermogram of a crystalline form E of valsartan disodium salts.
Figure 9:
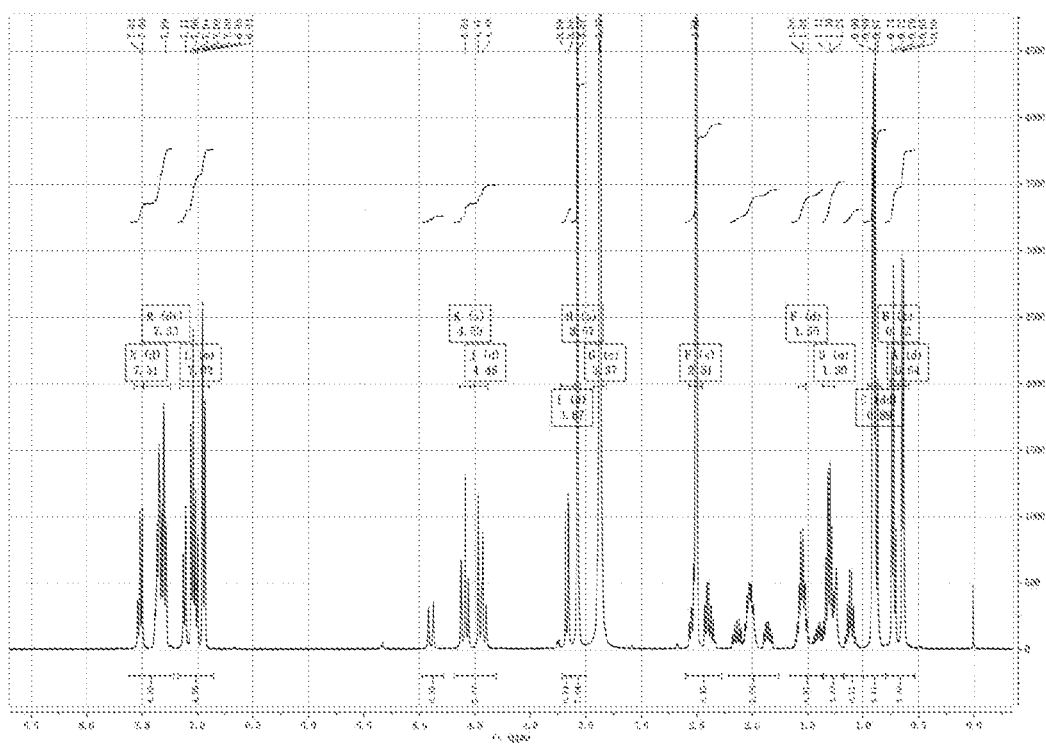
FIG. 9 shows a liquid-state nuclear magnetic resonance (H NMR) spectrum of a crystalline form E of valsartan disodium salts.
Figure 10:
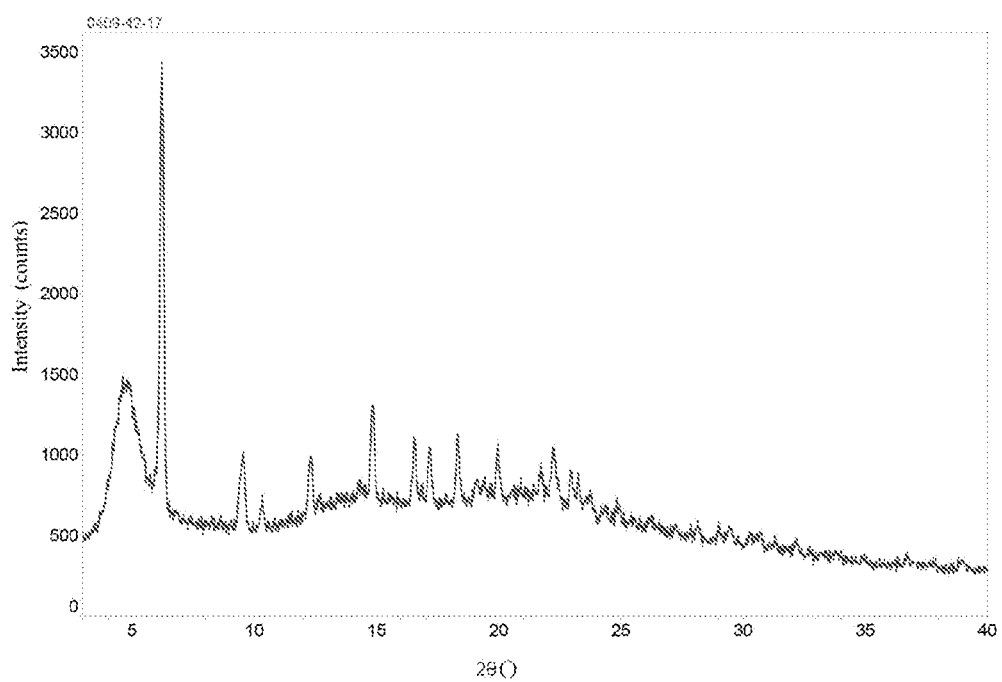
FIG. 10 shows an X-ray powder diffraction (XRD) pattern of a crystalline form F of valsartan disodium salts.
Figure 11:
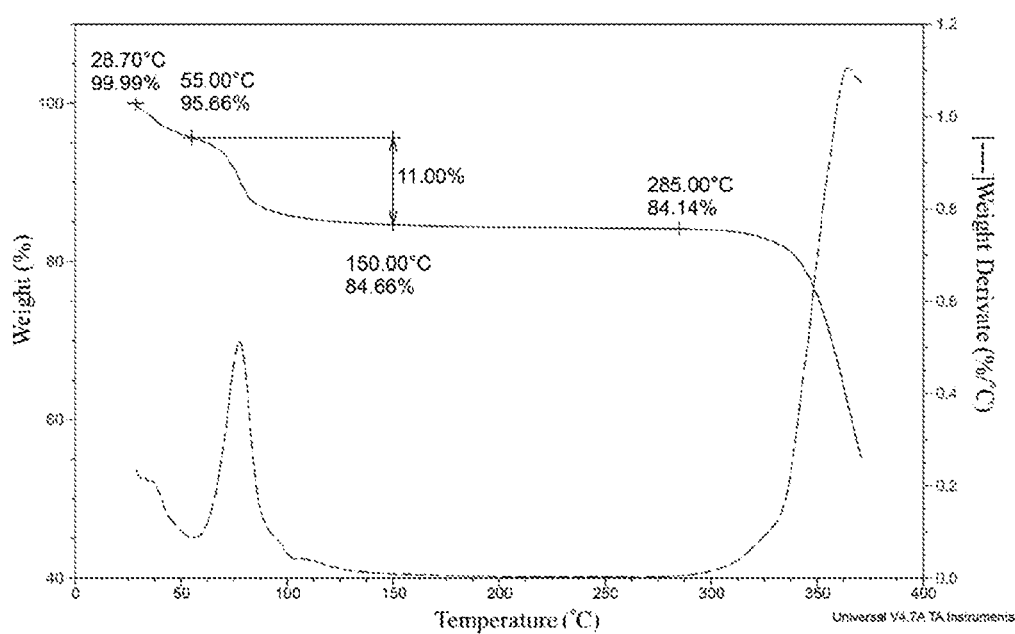
FIG. 11 shows a thermogravimetric analysis (TGA) plot of a crystalline form F of valsartan disodium salts.
Figure 12:
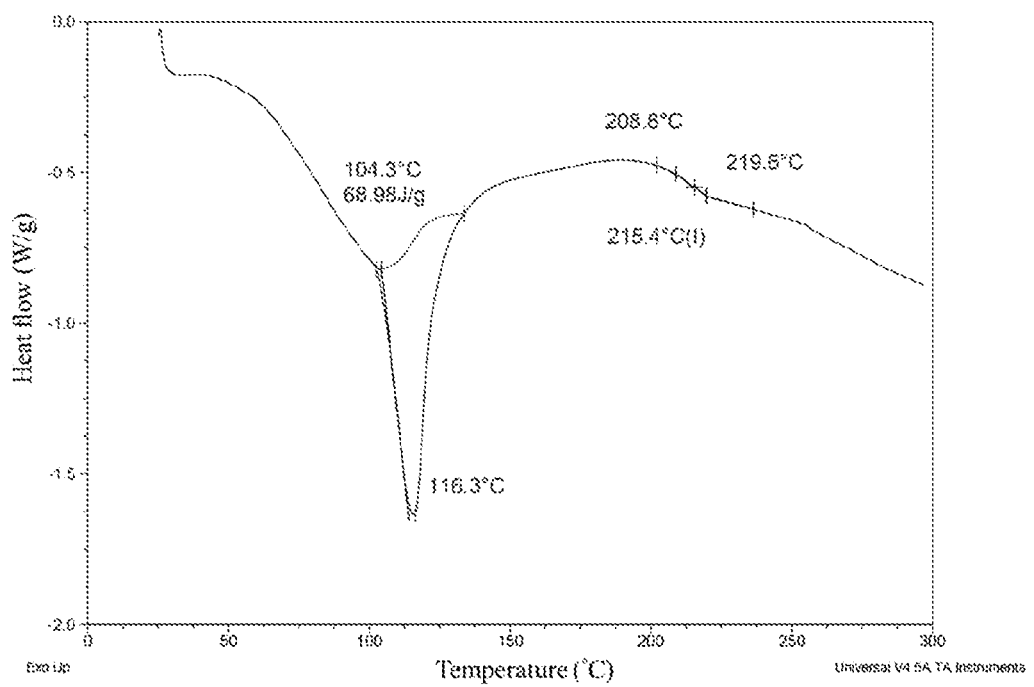
FIG. 12 shows a differential scanning calorimetry (DSC) thermogram of a crystalline form F of valsartan disodium salts.
Figure 13:
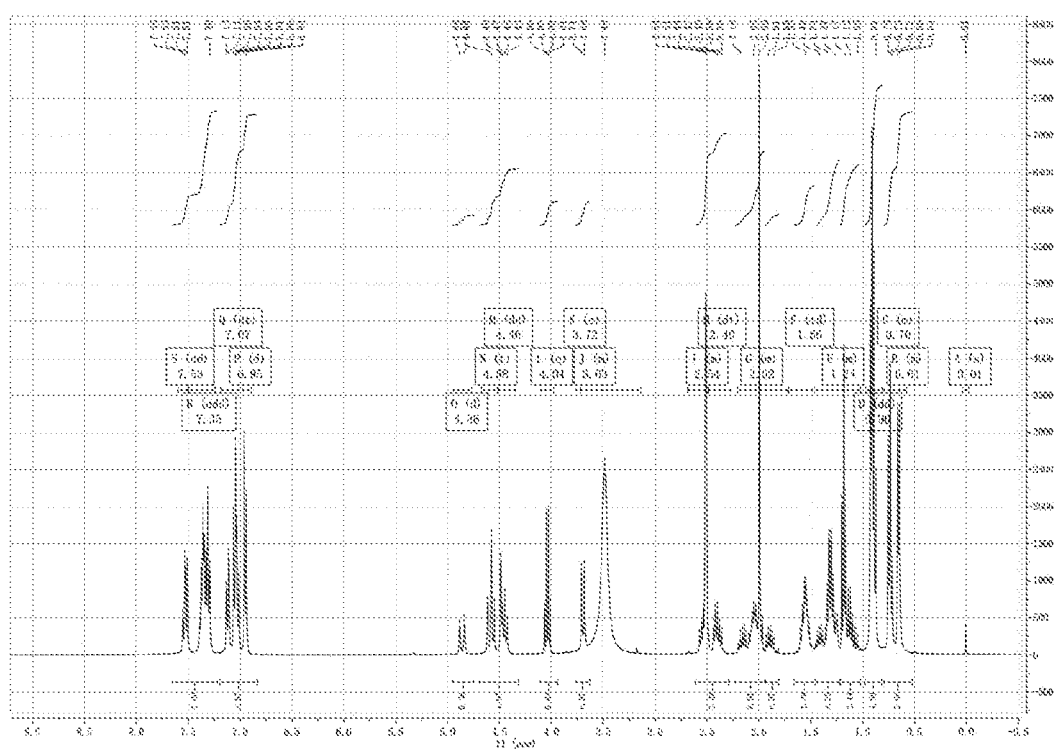
FIG. 13 shows a liquid-state nuclear magnetic resonance (H NMR) spectrum of a crystalline form F of valsartan disodium salts.
Figure 14:
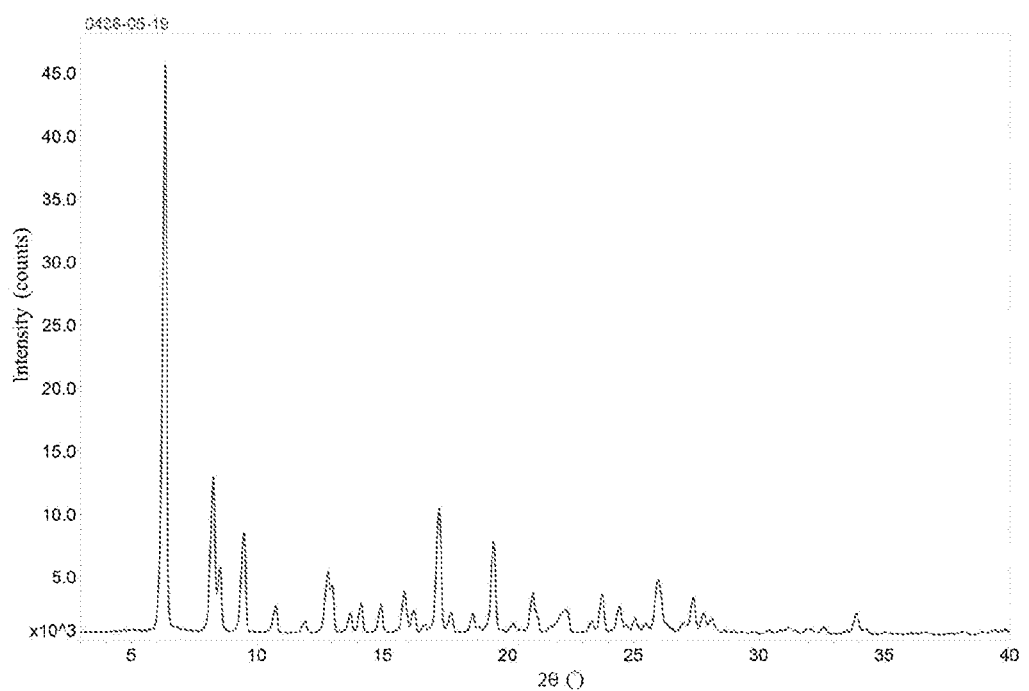
FIG. 14 shows an X-ray powder diffraction (XRD) pattern of a crystalline form G of valsartan disodium salts.
Figure 15:
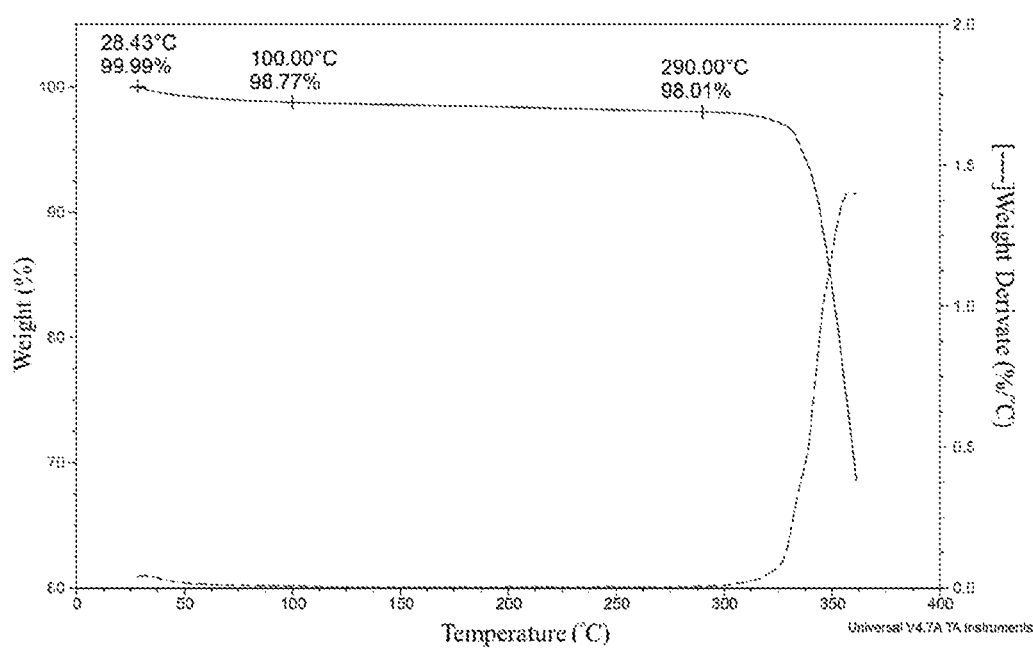
FIG. 15 shows a thermogravimetric analysis (TGA) plot of a crystalline form G of valsartan disodium salts.
Figure 16:
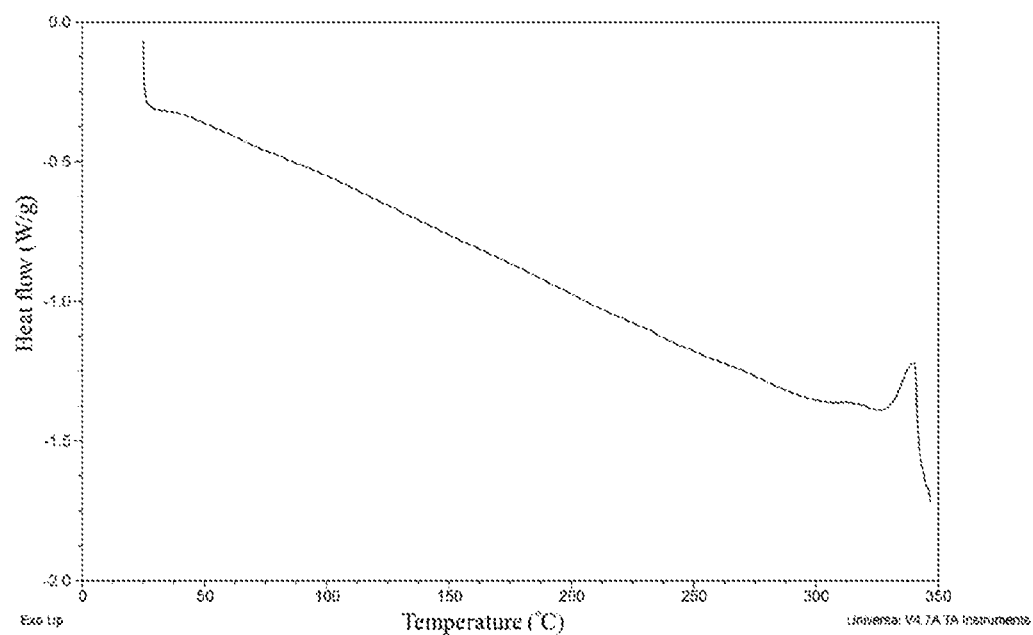
FIG. 16 shows a differential scanning calorimetry (DSC) thermogram of a crystalline form G of valsartan disodium salts.
Figure 17:
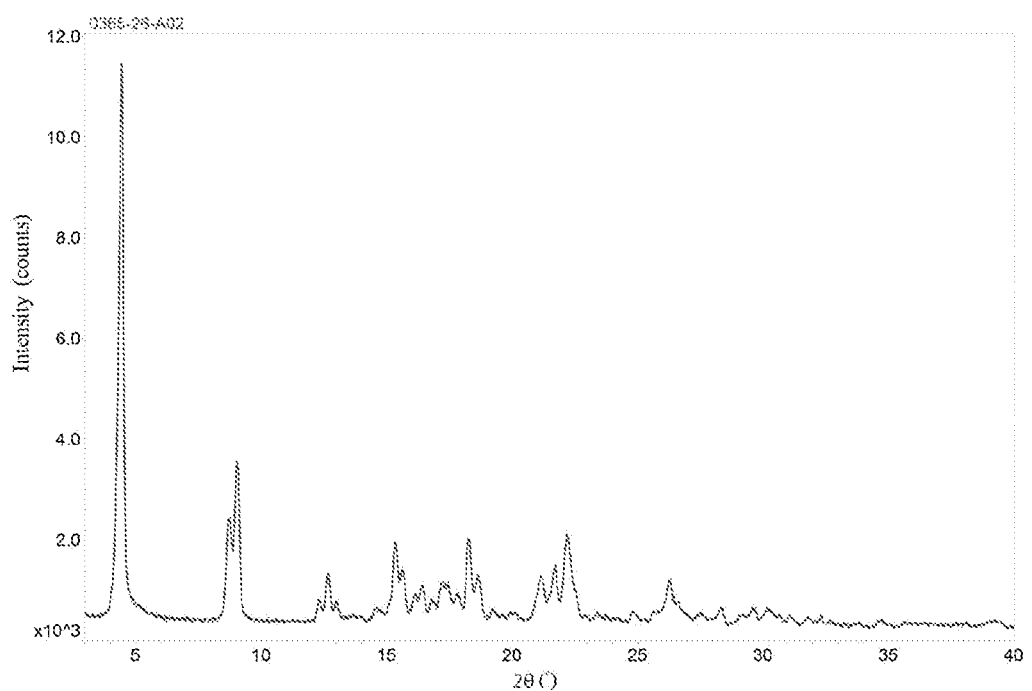
FIG. 17 shows an X-ray powder diffraction (XRD) pattern of a crystalline form H of valsartan disodium salts.
Figure 18:
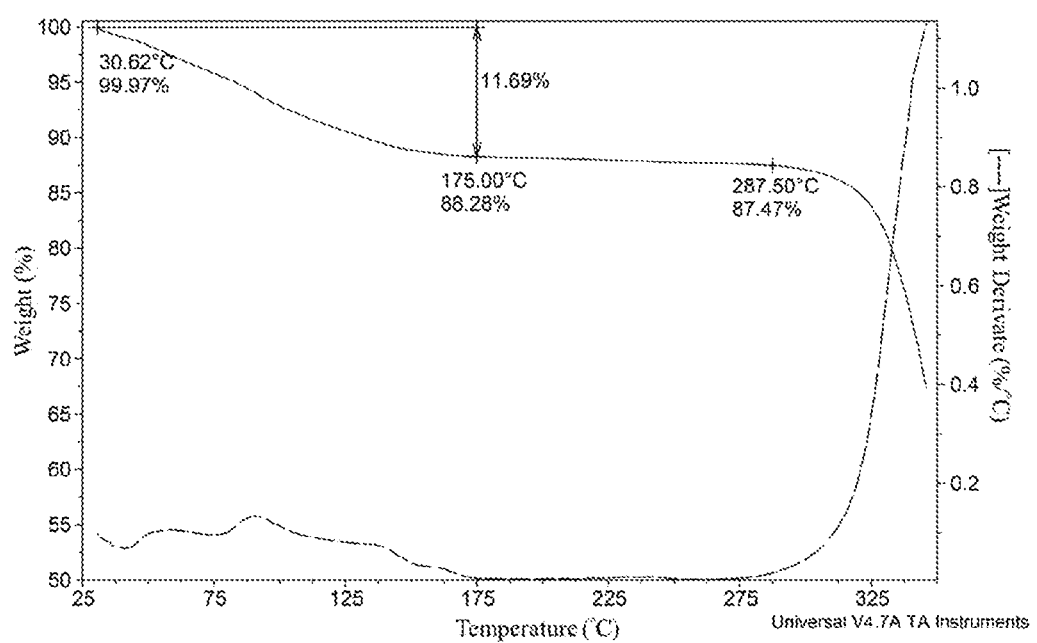
FIG. 18 shows a thermogravimetric analysis (TGA) plot of a crystalline form H of valsartan disodium salts.

The above summary of the present invention will be further described with reference to the embodiments of the following examples. However, it should not be understood that the content of the present invention is only limited to the following embodiments, and all the inventions based on the above-mentioned contents of the present invention belong to the scope of the present invention.

Example 1: Preparation of Crystalline Form A of Valsartan Disodium Salts 8.71 mg of valsartan was dissolved in 0.87 mL of isopropanol, and 0.2 mL of 2 mmol aqueous sodium hydroxide solution was added dropwise at room temperature. The mixture was stirred for 0.5 hour, and concentrated under reduced pressure to obtain a solid which was then stirred with n-heptane/ethanol (19/1, by volume) overnight, filtered, and vacuum dried at 40° C. to obtain a solid. 3 mg of the solid was added to 0.1 mL of methyl tert-butyl ether. After stirring for 72 hours, the supernatant was discarded after centrifugation, and the obtained solid was dried in an oven at 30° C. to yield a white solid, which is a type A valsartan disodium salt.

This valsartan disodium salt crystalline form A was subjected to a solid-state characterization by X-ray powder diffraction and differential scanning calorimetry. The solid-state characterization parameters and spectrums are as described herein.

Example 2: Preparation of Crystalline Form B of Valsartan Disodium Salts 10 mg of valsartan was added to 0.3 mL of water containing 1.84 mg of sodium hydroxide, and concentrated under reduced pressure to obtain a solid. 3 mg of the salt was added to 0.1 mL of 3-pentanone, and after stirring for 72 hours, the supernatant was discarded after centrifugation. The obtained solid was dried in an oven at 30° C. to yield a white solid, which is a type B valsartan disodium salt.

This valsartan disodium salt crystalline form B was subjected to a solid-state characterization by X-ray powder diffraction and thermogravimetric analysis. The solid-state characterization parameters and spectrums are as described herein.

Example 3: Preparation of Crystalline Form D of Valsartan Disodium Salts 8.71 mg of valsartan was dissolved in 0.87 mL of isopropanol, and 0.2 mL of 2 mmol of sodium hydroxide solution was added dropwise at room temperature. The mixture was stirred for 0.5 hour, and concentrated under reduced pressure to obtain a solid. The solid was stirred overnight with n-heptane/ethanol (19/1, by volume), filtered, and vacuum dried at 40° C. to obtain the valsartan disodium salt solid. 3 mg of the solid was added to 0.1 mL of n-heptane, and after stirring for 72 hours, the supernatant was discarded after centrifugation, and the obtained solid was dried in an oven at 30° C. to yield a white solid, which is a type D valsartan disodium salt.

This valsartan disodium salt crystalline form D was subjected to a solid-state characterization by X-ray powder diffraction. The solid-state characterization parameters and spectrums are as described herein.

Example 4: Preparation of Crystalline Form E of Valsartan Disodium Salts 8.71 mg of valsartan was dissolved in 0.87 mL of isopropyl alcohol, and 0.2 mL of 2 mmol of sodium hydroxide solution was added dropwise at room temperature. The mixture was stirred for 0.5 hour, and concentrated under reduced pressure to obtain a solid. The solid was stirred with n-heptane/ethanol (19/1, by volume) overnight, filtered, and vacuum dried at 40° C. to obtain a solid. 5 mg of the solid was added to 0.4 mL of 1,4-dioxane. After stirring for 48 hours, the supernatant was discarded after centrifugation, and the obtained solid was dried in an oven at 30° C. to yield a white solid, which is a type E valsartan disodium salt.

This valsartan disodium salt crystalline form E was subjected to a solid-state characterization by X-ray powder diffraction, thermogravimetric analysis, differential scanning calorimetry and liquid-state nuclear magnetic resonance. The solid-state characterization parameters and spectrums are as described herein.

Example 5: Preparation of Crystalline Form F of Valsartan Disodium Salts 8.71 mg of valsartan was dissolved in 0.87 mL of isopropyl alcohol, and 0.2 mL of 2 mmol of sodium hydroxide solution was added dropwise at room temperature. The mixture was stirred for 0.5 hour, and concentrated under reduced pressure to obtain a solid. The solid was stirred with n-heptane/ethanol (19/1, by volume) overnight, filtered, and vacuum dried at 40° C. to obtain a solid. 5 mg of the solid was added to 0.4 mL of ethyl acetate, and after stirring for 72 hours, the supernatant was discarded after centrifugation, and the obtained solid was dried in an oven at 30° C. to yield a white solid, which is a type F valsartan disodium salt.

This valsartan disodium salt crystalline form F was subjected to a solid-state characterization by X-ray powder diffraction, thermogravimetric analysis, differential scanning calorimetry and liquid-state nuclear magnetic resonance. The solid-state characterization parameters and spectrums are as described herein.

Example 6: Preparation of Crystalline Form G of Valsartan Disodium Salts 4.35 mg of valsartan was dissolved in 0.3 mL of acetone, and 0.1 mL of 2 mmol of sodium hydroxide solution was added dropwise. The mixture was stirred for 0.5 hour, and concentrated under reduced pressure. The obtained solid was recrystallized by 15 volumes of ethyl acetate to yield a white solid, which is a type G valsartan disodium salt.

This valsartan disodium salt crystalline form G was subjected to a solid-state characterization by X-ray powder diffraction, thermogravimetric analysis, and differential scanning calorimetry. The solid-state characterization parameters and spectrums are as described herein.

Example 7: Preparation of Crystalline Form H of Valsartan Disodium Salts 10 mg of valsartan was added to 0.3 mL of water, and 0.3 mL of 2 mmol of sodium hydroxide solution was added dropwise. The mixture was stirred for 0.5 hour, and concentrated under reduced pressure to obtain a solid. 0.2 mL of 2-butanone was added to 1 mg of the salt, and the mixture was stirred for 0.5 h, and refrigerated at 4° C. to precipitate a solid, which was dried in an oven at 0° C. to yield a white solid, which is a type H of valsartan disodium salt.

This valsartan disodium salt crystalline form H was subjected to a solid-state characterization by X-ray powder diffraction, thermogravimetric analysis and differential scanning calorimetry. The solid-state characterization parameters and spectrums are as described herein.

Example 8: Determination of Hygroscopicity of Each Valsartan Disodium Salt of the Present Invention Analysis Method:

1. Take a dry stuffed glass weighing bottle (outer diameter 50 mm, height 15 mm) in the artificial climate chamber (set temperature is 25±1° C., relative humidity is 43.5±2%) and weight it ($m_1$).

2. Take the appropriate amount of the crystalline form in the present invention, and place it in the abovementioned weighing bottle and lay it inside the weighing bottle. The thickness of the test sample is generally about 1 mm. Weight the sample ($m_2$).

3. Uncover the weighing bottle and place it with the bottle cap under constant temperature and humidity (set temperature is 25±1° C., relative humidity is 43.5±2%).

4. Put the cap back on the weighing bottle before weighing, and then weight it ($m_3$). The water absorption percentage for each time point is calculated by the formula=$(m_3-m_2)/(m_2-m_1)\times 100\%$.

Results:

TABLE 1

| Time | Crystalline form | Water absorption, % |
| --- | --- | --- |
| 2 h | A | 1.6% |
| 2 h | B | 1.9% |
| 2 h | D | 1.3% |
| 2 h | E | 2.1% |
| 2 h | F | 1.7% |
| 2 h | G | 0.7% |
| 2 h | H | 2.0% |
| 4 h | A | 2.0% |
| 4 h | B | 2.3% |
| 4 h | D | 1.9% |
| 4 h | E | 2.9% |
| 4 h | F | 2.2% |
| 4 h | G | 1.3% |
| 4 h | H | 2.8% |
| 24 h | A | 2.4% |
| 24 h | B | 3.0% |
| 24 h | D | 2.7% |
| 24 h | E | 3.6% |
| 24 h | F | 2.8% |

TABLE 1-continued

| Time | Crystalline form | Water absorption, % |
| --- | --- | --- |
| 24 h | G | 1.5% |
| 24 h | H | 4.0% |

From the hygroscopicity data shown in Table 1, the crystalline form of the valsartan disodium salt in the present invention has significantly improved hygroscopicity and is suitable for further development.

The above description merely relates to preferred embodiments in the present invention, and it should be pointed out that, for a person of ordinary skill in the art, some improvements and modifications can also be made under the premise of not departing from the principle of the present invention, and these improvements and modifications should also be considered to be within the scope of protection of the present invention.

What is claimed is:

1. Crystalline form B of valsartan disodium salt, wherein, the crystalline form has the following properties:
   by using a Cu-Kα radiation, its X-ray powder diffraction spectrum shows peaks at about 4.4±0.2 and 8.8±0.2, expressed in degree 2θ.

2. The crystalline form B of valsartan disodium salt according to claim 1, which has a melting point of about 198±5° C.

3. Crystalline form D of valsartan disodium salt, wherein, the crystalline form has the following properties:
   by using a Cu-Kα radiation, its X-ray powder diffraction spectrum shows peaks at about 4.4±0.2, 9.0±0.2, 14.9±0.2, 21.4±0.2, and 22.4±0.2, expressed in degrees 2θ.

4. The crystalline form D of valsartan disodium salt according to claim 3, which has a melting point of about 207±5° C.

5. Crystalline form E of valsartan disodium salt, which is a dioxane solvate, wherein, the crystalline form has the following properties:
   by using a Cu-Kα radiation, its X-ray powder diffraction spectrum shows peaks at about 6.3±0.2, 12.3±0.2, 14.7±0.2, 16.5±0.2, and 17.4±0.2, expressed in degrees 2θ.

6. The crystalline form E of valsartan disodium salt according to claim 5, wherein, at a heating rate of 10° C./min, a differential scanning calorimetry thermogram of said crystalline form E of valsartan disodium salt shows an endothermic peak at around 127° C.

7. The crystalline form E of valsartan disodium salt according to claim 5, wherein, at a heating rate of 10° C./min, a differential scanning calorimetry thermogram of said crystalline form E of valsartan disodium salt shows an endothermic peak at 107-127° C.

8. The crystalline form E of valsartan disodium salt according to claim 5, wherein, at a heating rate of 10° C./min, there is a thermal weight loss of said crystalline form E of valsartan disodium salt of not less than 15% at 64-200° C.

9. The crystalline form E of valsartan disodium salt according to claim 5, wherein, a ratio of valsartan disodium salt to dioxane in the crystalline form is 1:1.

10. Crystalline form F of valsartan disodium salt, which is an ethyl acetate solvate, wherein, the crystalline form has the following properties:
    by using a Cu-Kα radiation, its X-ray powder diffraction spectrum shows peaks at about 6.2±0.2, 14.9±0.2, and 18.3±0.2, expressed in degrees 2θ.

11. The crystalline form F of valsartan disodium salt according to claim 10, wherein, at a heating rate of 10° C./min, a differential scanning calorimetry thermogram of said crystalline form F of valsartan disodium salt shows an endothermic peak at around 116° C.

12. The crystalline form F of valsartan disodium salt according to claim 10, wherein, at a heating rate of 10° C./min, a differential scanning calorimetry thermogram of said crystalline form F of valsartan disodium salt shows an endothermic peak at 104-117° C.

13. The crystalline form F of valsartan disodium salt according to claim 10, wherein, at a heating rate of 10° C./min, there is a thermal weight loss of said crystalline form F of valsartan disodium salt of not less than 8.4% at 55-150° C.

14. The crystalline form F of valsartan disodium salt according to claim 10, wherein, a ratio of valsartan disodium salt to ethyl acetate in the crystalline form is 1:0.5.

15. Crystalline form G of valsartan disodium salt, wherein, the crystalline form has the following properties:
by using a Cu-Ka radiation, its X-ray powder diffraction spectrum shows peaks at about 6.4±0.2, 8.3±0.2, 9.5±0.2, 17.3±0.2, and 19.4±0.2, expressed in degrees 2θ.

16. The crystalline form G of valsartan disodium salt according to claim 15, wherein, at a heating rate of 10° C./min, degradation and melting signals in a differential scanning calorimetry curve overlap.

17. Crystalline form H of valsartan disodium salt, wherein, the crystalline form has the following properties:
by using a Cu-Ka radiation, its X-ray powder diffraction spectrum shows peaks at about 4.5±0.2, 8.7±0.2, and 9.0±0.2, expressed in degrees 2θ.

18. A pharmaceutical composition, comprising:
the crystalline form G of valsartan disodium salt according to claim 15; and
a pharmaceutically acceptable carrier.

19. A method for treating a disease or condition which is susceptible to treatment by blocking $AT_1$ receptor, comprising:
administering the crystalline form G of valsartan disodium salt according to claim 15 to a subject in need thereof, wherein the disease or condition comprises hypertension, congestive heart failure, acute renal failure, chronic renal failure, restenosis after percutaneous transluminal angioplasty, and restenosis after coronary artery bypass surgery; atherosclerosis, coronary heart disease, senile hypertension, and endothelial dysfunction with hypertension.

20. A pharmaceutical composition, comprising:
the crystalline form B of valsartan disodium salt according to claim 1; and
a pharmaceutically acceptable carrier.

21. A method for treating a disease or condition which is susceptible to treatment by blocking $AT_1$ receptor, comprising:
administering the crystalline form B of valsartan disodium salt according to claim 1 to a subject in need thereof,
wherein the disease or condition comprises hypertension, congestive heart failure, acute renal failure, chronic renal failure, restenosis after percutaneous transluminal angioplasty, and restenosis after coronary artery bypass surgery; atherosclerosis, coronary heart disease, senile hypertension, and endothelial dysfunction with hypertension.

22. A pharmaceutical composition, comprising:
the crystalline form D of valsartan disodium salt according to claim 3; and
a pharmaceutically acceptable carrier.

23. A method for treating a disease or condition which is susceptible to treatment by blocking $AT_1$ receptor, comprising:
administering the crystalline form D of valsartan disodium salt according to claim 6 to a subject in need thereof,
wherein the disease or condition comprises hypertension, congestive heart failure, acute renal failure, chronic renal failure, restenosis after percutaneous transluminal angioplasty, and restenosis after coronary artery bypass surgery; atherosclerosis, coronary heart disease, senile hypertension, and endothelial dysfunction with hypertension.

24. A pharmaceutical composition, comprising:
the crystalline form E of valsartan disodium salt according to claim 5; and
a pharmaceutically acceptable carrier.

25. A method for treating a disease or condition which is susceptible to treatment by blocking $AT_1$ receptor, comprising:
administering the crystalline form E of valsartan disodium salt according to claim 5 to a subject in need thereof,
wherein the disease or condition comprises hypertension, congestive heart failure, acute renal failure, chronic renal failure, restenosis after percutaneous transluminal angioplasty, and restenosis after coronary artery bypass surgery; atherosclerosis, coronary heart disease, senile hypertension, and endothelial dysfunction with hypertension.

26. A pharmaceutical composition, comprising:
the crystalline form F of valsartan disodium salt according to claim 10; and
a pharmaceutically acceptable carrier.

27. A method for treating a disease or condition which is susceptible to treatment by blocking $AT_1$ receptor, comprising:
administering the crystalline form F of valsartan disodium salt according to claim 10 to a subject in need thereof,
wherein the disease or condition comprises hypertension, congestive heart failure, acute renal failure, chronic renal failure, restenosis after percutaneous transluminal angioplasty, and restenosis after coronary artery bypass surgery; atherosclerosis, coronary heart disease, senile hypertension, and endothelial dysfunction with hypertension.

28. A pharmaceutical composition, comprising:
the crystalline form H of valsartan disodium salt according to claim 17; and
a pharmaceutically acceptable carrier.

29. A method for treating a disease or condition which is susceptible to treatment by blocking $AT_1$ receptor, comprising:
administering the crystalline form H of valsartan disodium salt according to claim 17 to a subject in need thereof,
wherein the disease or condition comprises hypertension, congestive heart failure, acute renal failure, chronic renal failure, restenosis after percutaneous transluminal angioplasty, and restenosis after coronary artery bypass surgery; atherosclerosis, coronary heart disease, senile hypertension, and endothelial dysfunction with hypertension.

* * * * *